United States Patent
Le

(10) Patent No.: US 11,918,669 B1
(45) Date of Patent: *Mar. 5, 2024

(54) EFFERVESCENT FOOT BATH AND METHOD

(71) Applicant: Michael Nghiem Le, Wichita, KS (US)

(72) Inventor: Michael Nghiem Le, Wichita, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/567,454

(22) Filed: Jan. 3, 2022

Related U.S. Application Data

(63) Continuation of application No. 16/029,356, filed on Jul. 6, 2018, now Pat. No. 11,213,469.

(60) Provisional application No. 62/529,853, filed on Jul. 7, 2017.

(51) Int. Cl.

| | |
|---|---|
| *A61K 8/362* | (2006.01) |
| *A61H 35/00* | (2006.01) |
| *A61K 8/02* | (2006.01) |
| *A61K 8/19* | (2006.01) |
| *A61K 8/25* | (2006.01) |
| *A61K 8/34* | (2006.01) |
| *A61K 8/55* | (2006.01) |
| *A61K 8/73* | (2006.01) |
| *A61K 8/81* | (2006.01) |
| *A61K 8/9794* | (2017.01) |
| *A61Q 19/10* | (2006.01) |

(52) U.S. Cl.
CPC ............ *A61K 8/362* (2013.01); *A61H 35/006* (2013.01); *A61K 8/0204* (2013.01); *A61K 8/19* (2013.01); *A61K 8/25* (2013.01); *A61K 8/34* (2013.01); *A61K 8/553* (2013.01); *A61K 8/732* (2013.01); *A61K 8/817* (2013.01); *A61K 8/9794* (2017.08); *A61Q 19/10* (2013.01); *A61K 2800/222* (2013.01)

(58) Field of Classification Search
CPC ........ A61K 8/362; A61K 8/0204; A61K 8/19; A61K 8/25; A61K 8/34; A61K 8/553; A61K 8/732; A61K 8/817; A61K 8/9794; A61K 2800/222; A61H 35/006; A61Q 19/10; A61F 13/06; A47K 7/026
See application file for complete search history.

(56) References Cited

U.S. PATENT DOCUMENTS

| | | | | |
|---|---|---|---|---|
| 5,100,674 A | * | 3/1992 | Ser | A61K 8/42 424/44 |
| 5,997,901 A | * | 12/1999 | Mills | A61L 9/01 424/464 |
| 11,213,469 B1 | * | 1/2022 | Le | A61K 8/8152 |
| 2002/0086039 A1 | * | 7/2002 | Lee | A61Q 3/00 424/401 |
| 2003/0059387 A1 | * | 3/2003 | Bergquist | A61Q 19/10 510/142 |
| 2004/0241130 A1 | * | 12/2004 | Tamareselvy | A61K 8/442 424/70.16 |
| 2005/0009017 A1 | * | 1/2005 | Kubota | A23L 11/07 536/123 |
| 2014/0255318 A1 | * | 9/2014 | Stasko | A61K 33/00 556/424 |
| 2015/0150813 A1 | * | 6/2015 | Koboshi | A61K 9/2013 424/700 |
| 2016/0143823 A1 | * | 5/2016 | Adams | A61Q 19/10 424/44 |
| 2019/0327961 A1 | * | 10/2019 | Remmal | A23B 7/157 |

* cited by examiner

*Primary Examiner* — Guy K Townsend
*Assistant Examiner* — Alessandro R Del Priore
(74) *Attorney, Agent, or Firm* — Robert O. Blinn

(57) ABSTRACT

An effervescent foot bath which employs an acid in combination with a carbonated base to produces a effervescing effect in a closed foot tub. The reaction has been designed to function externally to soften and begin the process of removing dry, rough peeling skin from the feet.

1 Claim, No Drawings

EFFERVESCENT FOOT BATH AND METHOD

CROSS REFERENCES TO RELATED APPLICATIONS

This application is a continuation of U.S. Non-Provisional patent application Ser. No. 16/029,356 filed on Jul. 6, 2018. U.S. Non-Provisional patent application Ser. No. 16/029,356 claimed the benefit of U.S. Provisional Patent Application Ser. No. 62/529,853 filed on Jul. 7, 2017, both of which are incorporated herein by reference.

FIELD

This invention relates to an effervescent foot bath and a method for using the same.

BACKGROUND

Footbaths are used in combination with pedicure treatments to soften and sooth the foot and facilitate various pedicure procedures. A footbath would provide improved results if the footbath were accompanied by vigorous bubbling action.

SUMMARY

The above described need is addressed by an effervescent foot bath which employs a mild acid in combination with a carbonated base to produces a effervescing effect in a foot tub. The reaction has been designed to function externally to soften and begin the process of removing dry, rough or peeling skin from the feet.

DETAILED DESCRIPTION

Generally, the effervescent pedicure foot bath is formulated by combining a low pH acid with a carbonated base to produce a vigorous effervescent medium. In the preferred embodiment, citric acid in a concentration between 0.1% and 65% is combined with chemically balanced amount of sodium bi-carbonate in a concentration also ranging between 0.1% and 65% to produce an actively effervescent foot bath. In the preferred embodiment, a first mixture comprising mostly citric acid powder is combined in a foot bath tub containing warm water with a second mixture comprising mostly sodium bicarbonate powder.

More particularly, for best results, the applicant has found that in a standard foot bath which begins with warm foot bath water, the attendant preferably adds an effective amount of citric acid and a corresponding balancing amount of sodium bicarbonate. Once these agents are added to the foot bath water, a vigorous effervescent reaction becomes immediately evident. The person receiving the pedicure may submerge at least one foot into the vigorously effervescent foot bath solution. Because the solution is generally pH balanced, the attendant is able to scrub the foot or feet thus submerged in the foot bath solution and perform various pedicure operations during the foot bath portion of the pedicure.

Concentrations and quantities may be varied within wide ranges and still be able to conduct a method which is within the scope of the invention. Moreover, while citric acid is preferred, for the foot bath solution an acid may be selected from a group consisting of: citric acid, formic acid, clutamic acid, ascorbic acid, L-ascorbic acid, all amino acids, sulfuric acid, muriatic acid, acrylic acid, methacrylic acid, hydrobromic acid, nitric acid, acetic acid, carbonic acid and phosphoric acid. Similarly, while sodium bicarbonate may be used as noted above, other bicarbonated bases may be selected.

One embodiment of the effervescent foot bath and method is a method which includes combining two mixtures from two packages (or containers or sources) in a foot bath tub containing at least one quart of mildly warm water or a quantity of warm water sufficient for submerging at least one foot of a person receiving a pedicure. In this embodiment, each of the first and the second mixture packages may contain approximately three ounces (85 g) of a powdered mixture by weight. In this one embodiment, the three ounce mixture packages are combined in a foot bath tub containing between 1 quart (approximately 1 liter) and 1 gallon (approximately 4 liters) or an amount of mildly warm water sufficient to submerge at least one foot of a foot bath recipient. The first package preferably contains a mixture of the following ingredients generally in the following percentage ranges by weight: (a) Citric Acid (powder form) 100% active, 87% to 95%, (I)) Menthol crystals 0.5% to 2.5%, (c) Lecithin (emulsifier) 0.2% to 0.7% (d) Polyquatemium 37 (a thickening polymer) 0.2% to 0.6% and (e) Aloe Vera (powder form) 0.1% to 0.4%. The second package preferably contains a mixture of the following ingredients generally in the following percentage ranges by weight: (a) Sodium Bicarbonate 90% to 96%, (b) Maltodextrin 4% to 8%, (c) Aloe Vera 0.1% to 1%, (d) Talc Powder 0.05% to 1%, and optionally, (e) Fragrance 0.03% to 1%. As can be seen from the above the primary ingredients are the citric acid and the sodium bicarbonate which will combine to cause an effervescent effect. The other ingredients noted above are present to provide favorable or desired product characteristics as are well known in the art. Once the contents of the packages are combined in warm water in a foot tub, a vigorous effervescent effect is noted. The pedicure recipient's feet may be placed in the foot bath tub and an attendant is able to proceed with various pedicure procedures and treatments.

The method for administering an effervescent foot bath of one embodiment of the foot bath and method could include the following steps: 1. Obtain a foot tub of warm water sufficient to submerge the feet of a pedicure recipient at least to the lower part of the ankle thus providing a foot tub of warm foot bath water. 2. Introduce the first mixture package as described above containing at least citric. 3. Add the second package described above that contains an effective amount of sodium bicarbonate. 4. Observe the effervescent reaction of the acid and the bicarbonate within the foot bath. 5. While the effervescent reaction observed in step 4, is occurring, submerge at least one foot of the pedicure recipient in the in the effervescent foot bath solution. And, 6. Perform pedicure procedures and treatments upon the foot or feet of the pedicure recipient either while the foot or feet are submerged in the effervescent foot bath or subsequent to such submersion.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. A method for treating the foot or the feet of a pedicure recipient in a foot bath, consisting of the following steps:

A. providing an amount of water in the foot bath that is sufficient for submerging at least one foot of a pedicure recipient,
B. obtaining two mixtures, each of the two mixtures being dry mixtures and each of the two mixtures being maintained in a separated fashion from each other, the two mixtures including;
(a) a first mixture consisting of at least 90% citric acid in powder form by weight, and: (i) between 0.5% and 2.5% menthol crystals, by weight (ii) between 0.2% and 0.7% lecithin (emulsifier), by weight (iii) between 0.2% and 0.6% Polyquaternium 37 by weight, and (iv) between 0.1% and 0.4%, aloe vera in powder form by weight, and,
(b) a second mixture consisting of at least 90% sodium bicarbonate in power form by weight in an amount sufficient such that when the citric acid reacts with the sodium bicarbonate the combined mixture in the foot bath has a pH between 3 and 10, the mixture that includes sodium bicarbonate also including: (i) between 4% and 8% maltodextrin by weight, (ii) between 0.1% and 1% aloe vera by weight, (iii) between 0.05% and 1% talc powder by weight, and, (iv) between 0.03% and 1% fragrance by weight,
(c) adding both the first mixture and the second mixture to the water of the foot bath to make an effervescent foot bath, the amount of citric acid in the first mixture and the amount of sodium bicarbonate in the second mixture being in relative proportions such that when the sodium bicarbonate has reacted with the citric acid in the foot bath, the resulting pH of the foot bath is between 3 and 10.

\* \* \* \* \*